United States Patent
Bluecher et al.

(10) Patent No.: US 11,672,635 B2
(45) Date of Patent: Jun. 13, 2023

(54) MICROSTRUCTURE SOFT TISSUE GRAFT

(71) Applicant: BVW Holding AG, Cham (CH)

(72) Inventors: Lukas Bluecher, Eurasberg (DE);
Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 144 days.

(21) Appl. No.: 16/862,531

(22) Filed: Apr. 29, 2020

(65) Prior Publication Data
US 2021/0338405 A1 Nov. 4, 2021

(51) Int. Cl.
*A61F 2/00* (2006.01)

(52) U.S. Cl.
CPC .... *A61F 2/0063* (2013.01); *A61F 2002/0068* (2013.01); *A61F 2210/0004* (2013.01); *A61F 2210/0076* (2013.01); *A61F 2220/0016* (2013.01); *A61F 2250/0031* (2013.01)

(58) Field of Classification Search
CPC ............ A61F 2/0063; A61F 2002/0068; A61F 2210/0004; A61F 2210/0076; A61F 2220/0016; A61F 2250/0031
See application file for complete search history.

(56) References Cited

U.S. PATENT DOCUMENTS

| | | | |
|---|---|---|---|
| 9,120,670 B2 | 9/2015 | Hulseman et al. | |
| 9,908,274 B2 | 3/2018 | Hulseman et al. | |
| 9,988,201 B2 | 6/2018 | Darin et al. | |
| 10,377,044 B2 | 8/2019 | Hulseman et al. | |
| 10,458,053 B2 | 10/2019 | Hulseman et al. | |
| 10,575,667 B2 | 3/2020 | Hulseman et al. | |
| 10,687,642 B2 | 6/2020 | Hulseman et al. | |
| 10,889,005 B2 | 1/2021 | Hulseman et al. | |
| 2003/0212460 A1* | 11/2003 | Darois ................... | A61F 2/0063 128/898 |
| 2005/0244455 A1* | 11/2005 | Greenawalt ............. | C08L 23/12 424/423 |
| 2006/0015143 A1* | 1/2006 | Alvarado ............... | A61F 2/0063 606/213 |
| 2008/0086216 A1* | 4/2008 | Wilson ................... | A61F 2/0063 623/23.74 |
| 2011/0238094 A1 | 9/2011 | Thomas et al. | |
| 2012/0065649 A1 | 3/2012 | Towler | |
| 2014/0148827 A1* | 5/2014 | Odermatt ............... | A61F 2/0063 606/151 |

(Continued)

FOREIGN PATENT DOCUMENTS

CA 2904415 A1 9/2014

OTHER PUBLICATIONS

Search Report and Written Opinion of corresponding International application No. PCT/US2021/028651, dated Aug. 6, 2021, 17 pages.

(Continued)

*Primary Examiner* — Jing Rui Ou
(74) *Attorney, Agent, or Firm* — Patterson Intellectual Property Law, P.C.; Ryan D. Levy; Mark A. Kilgore

(57) ABSTRACT

Soft tissue repair grafts are described comprising an anti-adhesion layer, a structural layer, and a localization layer. These layers may be distinct or integrated into one substrate. The term layer is used to distinguish tissue repair graft functionality rather than distinct material layers. The distinct layers of functionality may comprise a single plane of a substance.

14 Claims, 7 Drawing Sheets

(56) References Cited

U.S. PATENT DOCUMENTS

| | | |
|---|---|---|
| 2015/0305739 A1* | 10/2015 | Rolandi ................. A61B 17/08 606/221 |
| 2015/0368838 A1 | 12/2015 | Hulseman et al. |
| 2017/0014111 A1 | 1/2017 | Hulseman et al. |
| 2017/0095242 A1* | 4/2017 | Milbocker ......... A61B 17/0218 |
| 2017/0304040 A1* | 10/2017 | Greenhalgh ......... D04B 21/165 |
| 2018/0147321 A1 | 5/2018 | Bluecher et al. |
| 2018/0236511 A1* | 8/2018 | Milbocker .............. C23C 16/04 |
| 2019/0062155 A1 | 2/2019 | Hulseman et al. |
| 2019/0112186 A1 | 4/2019 | Jang et al. |
| 2019/0133222 A1* | 5/2019 | Milbocker .............. B32B 21/08 |
| 2020/0338808 A1 | 10/2020 | Hulseman et al. |
| 2021/0086371 A1 | 3/2021 | Hulseman et al. |

OTHER PUBLICATIONS

Tran Le-Giang et al; Bio-Inspired Barbed Microneedle for Skin Adhesion with Interlocking Mechanics; 2019 IEEE 32nd International Conference on Micro Electro Mechanical Systems (MEMS), IEEEE, Jan. 27, 2019; pp. 547-550.

* cited by examiner

MICROSTRUCTURE SOFT TISSUE GRAFT

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference: None

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to devices and methods in the field of soft tissue repair. More particularly, this invention pertains to graft materials for soft tissue repair that include an anti-adhesion layer that inhibits the formation of post-surgical adhesions and a fixation means that does not rely on sutures and advantageously self-adheres and distributes the anchoring force over a large tissue area.

Adhesions are fibrous bands of connective tissue that form between tissues and organs in the body that are not normally connected together, or that form in a way that is different from the normal connective tissue anatomy between tissues and organs in the body. Adhesions commonly form after surgery in the abdomen or the pelvic regions. In certain cases, adhesions may cause complications such as pain or obstruction of the organs to which they connect.

Adhesions generally begin forming shortly after surgery and may continue to develop thereafter. There are no known effective treatments to reverse adhesion formation. If adhesions lead to complications in the patient, the typical treatment is to remove them surgically. Thus, the best approach to adhesion management is prevention of adhesion formation, or limitation of adhesion formation, all together.

Although no known products for effectively reversing adhesion formation are known, various products for the prevention of adhesion formation exists and are commercially available. These products are not 100% effective, though their use is known to consistently reduce adhesion formation. These products take on many forms, such as gels and absorbable sheets that are applied to surgical sites within the body and are gradually resorbed over the course of a few days.

Sheets rather than gels are typically used in combination with a reinforcing mesh in the repair of soft tissue defects. Generally, the sheet is attached to the mesh as a composite structure. The sheet can be formed on the mesh or attached via adhesives. Normally, the mesh side of the composite structure faces a soft tissue defect, such as a hernia. It is advantageous to leave space between the mesh and anti-adhesion layer, to promote tissue ingrowth into the mesh and adhesion formation between the mesh and soft tissue defect. Optimally, the mesh acts as a tissue scaffold, promoting healthy rather than fibrotic tissue growth between mesh and soft tissue defect.

However, one disadvantage of the current products is the need to fixate the device in place using sutures or some similar mechanism. In products such as gels, which cannot be mechanically fixated to the tissue defect, the disadvantage is found in the poor ability to maintain the gel at the point of interest for a reasonably long-term period, such as hours, days, or weeks. Thus, some products have good fixation through mechanical means, but have poor repositionability and create injury to the surrounding tissues, while other products are repositionable but have poor long-term positionability.

Therefore, a repositionable, self-adhering repair graft is needed for placement at a location of interest that may maintain its positioning but does not require mechanical fixation. Further, there is a need for a device with a repositionable characteristic having an adhesion strength adequate to maintain the device temporarily in place, otherwise unsupported, against the tissue of a targeted tissue location during a surgical procedure, and in the absence of a positioning agent requiring setting or curing.

BRIEF SUMMARY

In accordance with the present disclosure, various embodiments are described herein. In some embodiments, a positioning agent may be provided on a soft tissue repair graft. The positioning agent may possess an adherence capability adequate to temporarily maintain a surgical soft tissue repair prosthesis in place, otherwise unsupported, against a targeted tissue location during a surgical procedure. In some embodiments, the mesh prosthesis may be maintained in the temporary position until the mesh prosthesis is permanently fixed in place against the targeted tissue location using a device for permanent fixation. In some embodiments, a device for permanent fixation may include sutures, surgical tacks, surgical staples, and the like. The positioning agent may exhibit sufficient adherence capability when applied to the surgical soft tissue repair prosthesis to hold it in place against gravity, for example, in the absence of setting or curing of the positioning agent during the implantation procedure.

Embodiments of the present disclosure may include a permanent fixation agent provided on a soft tissue repair graft. In some embodiments, a positioning agent may work in combination with the permanent fixation agent, and together they possess an adherence capability adequate to maintain a surgical soft tissue repair prosthesis in place, otherwise unsupported, against a targeted tissue location during a surgical procedure. In some embodiments, the soft tissue repair graft may be permanently fixated by applying a normal force to the soft tissue repair prosthesis to complete the action of the fixation agent, wherein the positioning and fixation agents exhibit sufficient adherence capability when applied to the surgical soft tissue repair prosthesis to hold it in place against gravity, for example, in the absence of setting or curing of the positioning agent during the implantation procedure. In some embodiments, the fixation agent may provide sufficient fixation to keep the soft tissue repair prosthesis in place for a specified amount of time such that adhesion formation between the target tissue surface and the mesh layer of the soft tissue repair prosthesis is limited.

Embodiments of the present disclosure may include a method of implanting a surgical mesh prosthesis, wherein the method may include the steps of positioning a surgical mesh prosthesis against a surface of a target tissue with a positioning agent disposed between the mesh layer of the prosthesis and the surface of the target tissue. The positioning agent may include an adherence capability adequate to maintain the mesh layer temporarily in place against gravity, otherwise unsupported, against the target tissue in the absence of setting or curing of a positioning agent. In some embodiments, the positioning agent may be applied to the surface of the target tissue before positioning the surgical mesh prosthesis against the surface of the positioning agent. In some embodiments, the positioning agent may be applied to a first side of the surgical mesh prosthesis before positioning the surgical mesh prosthesis against the surface of the target tissue. This method may further include repositioning the surgical soft tissue repair prosthesis from a first location on the tissue to a second location on the tissue. In some embodiments, the method may further include peeling the surgical soft tissue repair prosthesis away from a first location on the tissue and placing the surgical soft tissue repair prosthesis in a second location on the tissue without traumatizing or damaging the tissue.

Embodiments of the present disclosure may include an implantable device that has an anti-adhesion layer, a tissue scaffold layer, a positional layer, and a permanent fixation layer. In some embodiments, one of the layers may be combined with another while both layers retain their capabilities and/or characteristics.

Embodiments of the present disclosure may include a soft tissue repair graft comprising a first layer stacked onto a second layer stacked, and the second layer stacked onto a third layer. In some embodiments, the first layer may comprise a mesh formed of a non-absorbable polymeric material. The second layer may comprise a barrier layer formed of an absorbable or non-absorbable polymeric material. And the third layer may comprise an absorbable or non-absorbable polymeric layer whereon a first pattern is disposed onto the polymeric layer with a bioabsorbable material and whereon a second pattern is disposed comprising the same polymer as comprising the third layer. In some embodiments, the second layer may have a first surface that is adjacent the bowels of a patient. The third layer may have a first surface that is adjacent to tissue comprising a defect. In some embodiments, the first surface of the third layer may be in contact with the tissue comprising a defect. In some embodiments, the first layer may be flexibly attached to the second and third layers. In some embodiments, the first pattern of the third layer may create an orthogonal attractive force that attracts the tissue facing side of the third layer to the tissue with force sufficient to drive the second pattern of the third layer into the tissue so as to affix the soft tissue repair graft to the tissue.

Embodiments of the present disclosure may include a soft tissue repair graft wherein the first layer is non-absorbable, the second layer is absorbable, and the third layer is non-absorbable.

Embodiments of the present disclosure may include a soft tissue repair graft wherein the first layer is non-absorbable, the second layer is non-absorbable, and the third layer is absorbable.

Embodiments of the present disclosure may include a soft tissue repair graft wherein a first pattern may include a microstructure capable of generating at least one of a) a capillary attractive force, b) a van der Waals attractive force, c) a Wenzel-Cassie interface, d) a Schallamach capturing interface, e) an eigenwrinkle capturing interface, and f) an ingrowth surface.

Embodiments of the present disclosure may include a soft tissue repair graft wherein a first pattern may include a hierarchically arranged microstructure comprising at least two surface sub-patterns of different surface energy. In some embodiments the first sub-pattern may be of higher surface energy and become hydrophilic and the second sub-pattern may be of lower surface energy and become hydrophobic when said first layer is brought into contact with an aqueous-wet surface.

Embodiments of the present disclosure may include a soft tissue repair graft wherein an attractive force generated by a first pattern is insufficient to drive a second pattern completely into a tissue layer. Such a configuration and cooperation between the first and second patterns may provide the soft tissue repair graft with the ability to be repositioned without tissue damage. In some embodiments, when an ideal graft position is realized, a slight normal force generated by a clinician may the engage the second pattern with the tissue layer. In some embodiments, the normal force applied by a clinician may further engage the second pattern which may already be at least partially engaged with the tissue layer.

Embodiments of the present disclosure may include soft tissue repair graft wherein a second pattern is comprised of barbs, or suitably tissue adherent structures which resists removal from said tissue layer when said second pattern is invasively engaged into the tissue layer by the first pattern or by external force.

Embodiments of the present disclosure may include a soft tissue repair graft wherein the second pattern is designed to maximally distribute the soft tissue repair graft fixation force over the area of contact after implantation. In some embodiments, the soft tissue repair graft may be detached from contact with the target surface. In some embodiments, the target surface may be in contact with the uppermost microfeature of a hierarchical microstructure, but not in direct contact with other microfeatures of the hierarchical microstructure. During detachment, a single uppermost microfeature of a hierarchical microstructure may not exert a force on the target surface of greater than 0.025 $kg/cm^3$, and wherein the volume ($cm^3$) may be the volume of the single uppermost microstructural element. In some embodiments, the force required to completely detach the soft tissue repair graft from the target surface may be greater than 25 $kg/cm^2$, wherein the surface area ($cm^2$) may be the contact area between the soft tissue repair graft and tissue layer.

In some embodiments, during detachment, a single hierarchical microstructure may not exert a force on the target surface of greater than 0.025 $kg/cm^3$, and wherein the volume ($cm^3$) may be the volume of the individual microfeatures that are arranged hierarchically.

In some embodiments, during detachment, a single microfeature, which is not hierarchical, may not exert a force on the target surface of greater than 0.025 $kg/cm^3$, and wherein the volume ($cm^3$) may be the volume of the microfeature. In some embodiments, the single microfeature may be a barbed microfeature. In some embodiments, the barbed microfeature may also be the uppermost microfeature of a hierarchical microstructure.

Embodiments of the present disclosure may include a soft tissue repair graft may include microstructure elements of a second pattern being at least 50% longer than the longest microstructure elements of a first pattern.

Embodiments of the present disclosure may include a soft tissue repair graft having a third layer being fenestrated to allow tissue growth from the tissue, through the third layer, and into a second layer.

Embodiments of the present disclosure may include a soft tissue repair graft having a first layer being a mesh with open cell pores of between 0.5 mm and 6 mm in diameter.

Embodiments of the present disclosure may include a soft tissue repair graft having the mesh formed of a warp knitted filament and wherein the diameter of the filament is between 5 microns and 100 microns.

Embodiments of the present disclosure may include a soft tissue repair graft having a mass per unit area being less than 300 $g/m^2$.

I Embodiments of the present disclosure may include a soft tissue repair graft comprising a self-adhering layer, a prosthetic reinforcing layer, and an anti-adhesion layer, the graft configured to repair animal tissue. In some embodiments, each layer may be combined with another layer but each layer may retain its characteristics. In some embodiments, the soft tissue repair graft may include a sheet of absorbable surgical barrier, a sheet of mesh material, and a sheet of adhesive material, wherein the adhesive sheet may include at least first and second microstructures. In some embodiments, the adhesive sheet may include a plurality of fenestrations that allow for adherence between a defective tissue surface and the sheet of mesh, wherein all three sheets are flexibly joined, allowing up to mm lateral displacement between sheets.

Embodiments of the present disclosure may include a soft tissue repair graft wherein the three joined sheets may include a preformed and nesting shape that substantially departs from a plane.

Embodiments of the present disclosure may include a soft tissue repair graft comprising two membranes, one membrane configured to promote fixation and tissue ingrowth and a second membrane to prevent fixation and tissue ingrowth. In some embodiments, liquid adhesive or tissue bonding agent is absent on the membranes. In some embodiments, a mesh may be disposed between the membranes having a mean pore size of between 100 and 2000 microns. In some embodiments, the soft tissue repair graft may adhere to a defective tissue layer on contact.

Embodiments of the present disclosure may include a soft tissue repair graft wherein an adhesion blocking gel layer may replace the membrane layer for preventing fixation and tissue ingrowth.

Embodiments of the present disclosure may include a soft tissue repair graft wherein the membrane for promoting fixation and tissue ingrowth may include a hierarchical microstructure portion and a tissue engagement portion.

Embodiments of the present disclosure may include a soft tissue repair graft wherein the self-adhering layer is a combination of an attractive force created by a hierarchical microstructure first portion and a tissue-penetrating and retaining second portion, wherein the first portion causes fixation of the second portion.

DETAILED DESCRIPTION OF THE INVENTION

Figure 1:
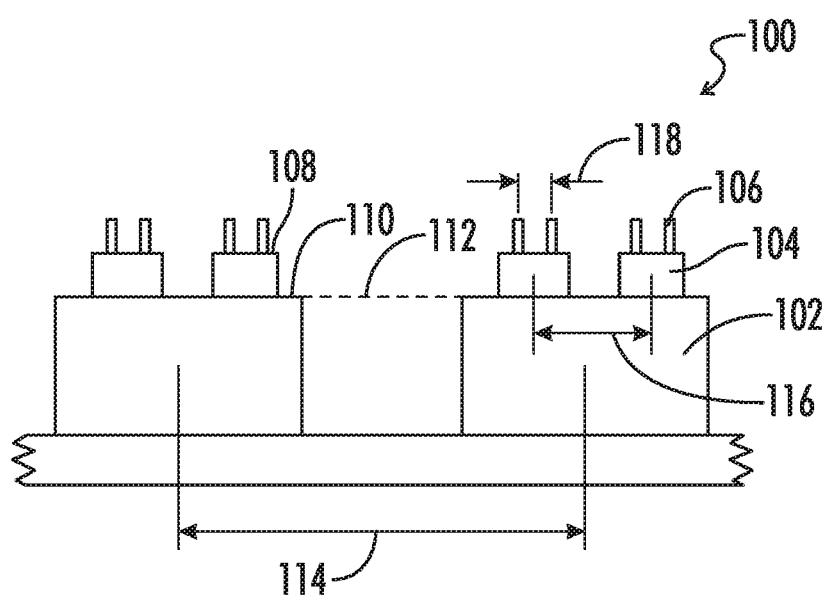
FIG. 1 is an embodiment of hierarchical microstructures demonstrating a branching ratio.

Reference will now be made in detail to the embodiments of the present disclosure, one or more examples of which are set forth herein below. Each embodiment and example is provided by way of explanation of the device, composition, and materials of the present disclosure and is not a limitation. Rather, the following description provides a convenient illustration for implementing exemplary embodiments of the disclosure. In fact, it will be apparent to those skilled in the art that various modifications and variations can be made to the teachings of the present disclosure without departing from the scope or spirit of the disclosure. For instance, features illustrated or described as part of one embodiment, can be used with another embodiment to yield a still further embodiment. Thus, it is intended that the present disclosure covers such modifications and variations as come within the scope of the appended claims and their equivalents. Other objects, features, and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

Exemplary applications of apparatuses and methods according to the present disclosure are described in this section. These examples are being provided solely to add context and aid in the understanding of this disclosure. It will thus be apparent to one skilled in the art that the present disclosure may be practiced without some or all of these specific details. In other instances, well known process steps have not been described in detail in order to avoid unnecessarily obscuring the present disclosure. Other applications are possible, such that the following examples should not be taken as limiting.

In the following detailed description, references are made to the accompanying drawings, which form a part of the description and in which are shown, by way of illustration, specific embodiments of the present disclosure. Although these embodiments are described in sufficient detail to enable one skilled in the art to practice the invention, it is understood that these examples are not limiting; such that other embodiments may be used, and changes may be made without departing from the spirit and scope of the disclosure.

As used herein, the term "intersurface adhesion" may be understood to describe the adhesion formed between a microstructured surface and a contact surface. It will be understood that the term may apply to resistance of lateral translation (shear) and resistance of normal translation (peel). The term may also be applied to suction forces generated when the surface tension of the liquid and the surface energy of the microstructured surface form an interface in which the energy of both are minimized.

As used herein, the term "fractal dimension" as applied to a microstructured surface may be understood to describe a microstructured surface with a characteristic branching ratio.

As used herein, the term "Wenzel-Cassie interface" may be understood to refer to an interfacial volume formed between two solid surfaces. The interfacial volume may contain at least two fluids of different surface energies. It will be understood that "fluid" may refer to either a liquid or a gas, or both.

As used herein, the term "surface energy" may be understood to refer to the potential energy of surface molecules per unit area of a surface. The term "surface energy gradient" as used herein may be understood to refer to the variation of a spatial derivative of the surface energy along a path joining two surfaces.

The organization of the interfacial volume in a Wenzel-Cassie interface may be understood to be a minimization of surface energy gradients of the hierarchically microstructured surface and the liquid components of the Wenzel-Cassie interface. Accordingly, interfacial liquids and surface microstructures may generally associate in pairs, where the sum of the surface energy differences of each of the liquid-microstructure pairs may be a minimum.

As used herein, the term "surface tension" may be understood to describe the surface energy of liquids. Surface tension may be understood as the amount of work done in increasing the area of the liquid surface by unity against the force of surface tension at constant temperature.

It will be understood by those skilled in the art that many of these phenomena may emerge over time, in some cases on the time period of minutes. Thus, a first microstructured surface that generates a Wenzel-Cassie interface may reduce the distance between the microstructure surface and the contact surface over time. If a second microstructure is utilized in combination with the first microstructure, and the second microstructure is has a greater length than the first microstructure and designed to mechanically engage soft tissue, then the first microstructure may serve to drive the second tissue engaging element(s) into the soft tissue contact surface.

As used herein, the term "positional strength" may be understood to include a general term for the self-adherent properties of a microstructured surface due to Van der Waals interactions. Generally, positional strength may be associated with a Wenzel-Cassie interface. Positional strength may be understood as a contact surface-noninvasive adherence characterized by force per unit area. Positional strength may be quantified in this disclosure in two ways: translational (shear) adherence, and peel (lift) adherence.

As used herein, the term "areal ratio" may be understood to refer to the porosity of a material, including, but not limited to, a mesh or sheet. Areal ratio may be the ratio of the porous area of the material divided by the total area of the sheet. Sheets of decreasing areal density may be understood to have increasing porosity.

As used herein, the term "barb" may be understood to refer to any microfeature on a surface which may be intended to invasively engage a contact surface. In some embodiments, the barbs may be smooth tapered pillars, or pillars arranged with arrowhead-like structures.

As used herein, the term "invasive" may be understood to refer to the penetration of at least a portion of an object into a surface.

The present disclosure relates to novel materials for soft tissue repair, and in particular, materials for hernia repair. These novel materials may be configured in a variety of applications, including, but not limited to, as an implant, such as a graft or soft tissue support device. These materials may be implanted into a patient such as one having a hernia or undergoing a hernia repair surgical procedure.

Advantageously, these materials (and any apparatuses such as devices and systems, including grafts, that utilize these materials) are particularly well suited for surgical implantation over time in repair of a body wall cavity, and may have advantageous biomechanical or biochemical properties over those devices and materials of the prior art. In particular, the compliance of any device permanently fixed to a target tissue should match the compliance of the target tissue so as to generate the best outcomes and minimize complications from the surgery. Conversely, the compliance should be sufficient to correct the tissue defect, at least after the passage of time. Consequently, many biomechanical features of prior art implant devices represent compromises between biocompatibility and therapy, and therefore are inadequate.

Similarly, it is generally true that the addition of a surgical barrier to a surgical scaffold may cause the combined device to become stiffer. On the other hand, adhesion formation generally does not occur after 7 days post-operatively. Therefore, the surgical barrier may be absorbable after a given time period.

In some embodiments, the apparatus of the present disclosure may comprise a tissue scaffold material. In some embodiments, the tissue scaffold material may be a mesh. The scaffold material may be a biotextile, medical textile, or both a biotextile and medical textile. In some embodiments, the apparatus may also include an anti-adhesion layer that may be attached to the tissue scaffold material. In some embodiments, the anti-adhesion layer may be located at discrete locations on the scaffold material. It will be understood that "discrete" as used herein may be understood to include the anti-adhesion layer being at a separate and distinct location(s) on the scaffold material, and therefore not disposed about the entire surface area of the scaffold material. In some embodiments, the location may include the anti-adhesion layer being incorporated into the scaffold material and/or it may be fastened onto the scaffold material. In some embodiments, the anti-adhesion layer may be fastened onto the scaffold material while still allowing sliding between the scaffold material and the anti-adhesion layer at regions adjacent and/or between the discrete anti-adhesion locations.

The tissue scaffold may be comprised of a variety of materials and/or compositions. In some embodiments, the tissue scaffold material may be biocompatible. In some embodiments, the scaffold material may include an extracellular matrix, a hernia repair scaffold, a patch, and/or a mesh, or the like. The tissue scaffold may be arranged in an open-cell geometry, and in some embodiments may be referred to herein as a "mesh". In some embodiments, the mesh may be biocompatible, and/or bioabsorbable, and/or non-bioabsorbable. In some embodiments, the tissue scaffold may include a biocompatible film. Throughout this application, the tissue scaffold material may be referred to collectively as a first layer, regardless of whether the tissue scaffold is made up of many sublayers such as a mesh and film together, or just a single layer.

Embodiments of a tissue scaffold may be formed of a material that is non-bioabsorbable. In some embodiments, these non-bioabsorbable materials may include a filament that is incorporated into the material. In some embodiments, the filament may be thread, wire, braid, monofilament, multi-filament, a combination thereof, or the like. In some embodiments, the filament may be incorporated by a method similar to weaving, sewing, or embroidering the filament into the tissue scaffold material. In some embodiments, the incorporation of a filament may include producing a pattern within the scaffold material. A first pattern may be incorporated utilizing a non-bioabsorbable filament material wherein the first pattern may be a grid or array of lines that are substantially parallel. In some embodiments, the first pattern may comprise a plurality of sub-patterns that are arranged offset from each other and/or overlapping which together may create a larger pattern. The filament material forming the first pattern, and/or the overall first pattern, may have a lower compliance than the mesh. Thus, the final compliance of the tissue scaffold may be the compliance of the mesh and the first pattern incorporated into the mesh.

In some embodiments, a second filament may be used along with, or in conjunction with, the first filament. The second filament may include a different filament material than the first filament. In some embodiments, the second filament may be used along with the first filament to create the first pattern. In other embodiments the first filament may create a first pattern and the second filament may create a second pattern. It will be understood by one of skill in the art that any number of filaments and patterns may be used. It will also be understood that a single filament material may be used to produce a single pattern and/or multiple patterns. And multiple filament materials may be used to produce a single pattern and/or multiple patterns.

In some embodiments wherein the mesh is bioabsorbable, a filament material that is bioabsorbable may also be used. In some embodiments, the bioabsorbable material of the mesh and the bioabsorbable material of the filament may have similar absorbability profiles such that each material is absorbed at approximately the same rate in the same environment. In some embodiments, the filament material may include a different bioabsorbable profile such that the filament is absorbed more quickly than the mesh material, or it may be absorbed more slowly. In a preferred embodiment, the filament material is absorbed more quickly than the mesh bioabsorbable material.

The compliance (e.g., flexural modulus) of a material may refer to the mechanical property of the material undergoing elastic deformation when subjected to an applied force. It may be understood as the reciprocal of stiffness. Compliance may be described as a percent compliance strain. Materials that deform easily are said to be compliant and materials that resist deformation are considered to be stiff.

Some embodiments of the present disclosure may include an anti-adhesion layer. In some embodiments, the anti-adhesion layer may include one or more layers of an anti-adhesion material. It should be noted that reference to an "anti-adhesion layer" does not necessarily denote that the layer or material is "non-adhesive" but rather is a layer or material that prevents or substantially limits the formation of "adhesions."

In some embodiments, the anti-adhesion material may include one or more layers of the biotextile and/or medical textile. In some embodiments, the material may preferably be an extracellular material, such as extracellular matrix derived from one or more of the dermis, pericardium, peritoneum, intestine, stomach, or forestomach. It will be understood in this disclosure, the anti-adhesion layer may also be referred to as a "second layer." However, reference to a "second layer" is not limited solely to an anti-adhesion layer.

Embodiments of the present disclosure may include a first layer (tissue scaffold material) with a second layer (anti-adhesion layer) being attached to the first layer. In some embodiments, the combination of layers is configured in a manner that does not substantially change the compliance of the first layer. In practice, this may mean that the compliance of the first and second layers separately or when combined, is not changed more than a few percent when attached together as described herein.

Some embodiments of the present disclosure may include a first and second layer attached together wherein the compliance of the material when the first and second layers are attached together at discrete attachment sites may be within 20% or less of the compliance of either the first layer alone or the second layer alone, or a combination of the first and second layers when "stacked" on top of one another, but not attached. It may be understood that "discrete" as used herein for "discrete attachment sites" may mean each location where the first and second layers is attached to each other is individually separate and distinct from another location. The discrete attachment sites may be any number of methods for attaching the first layer and the second layer. In some embodiments, the discrete attachment sites may include stitches connecting the first layer to the second layer. In some embodiments, the site may be chemical or polymeric adhesives between the two layers in small, discrete locations, such as an adhesive or glue material that is biocompatible and adheres the first layer to the second layer. The adhesive may be any appropriate biologically compatible adhesive.

In some embodiments, the discrete attachment sites may include relatively small diameter regions which may be regularly shaped or irregularly shaped. Embodiments which include stitches as the discrete attachment site may include a material woven or stitched between the two layers, and the discrete attachment sites may have a diameter of the stitching material. The stitching material may be selected from a filament, thread, yarn, or the like. The stitching material may be biocompatible and/or bioabsorbable. In some embodiments, the discrete attachment sites may have a diameter of between about 1 micron and 10 mm.

Embodiments of the present disclosure may include an anti-adhesion layer being connected to a tissue scaffold material wherein the anti-adhesion layer may be connected to the scaffold via weaving of a material connecting the layers together. In some embodiments, the weaving of the material may comprise a stitch pattern that may include at least one filament, thread, or yarn comprising an anti-adhesion material. It will be understood that stitch patterns as described herein may be patterns of discrete attachment sites that may be arranged in an overall pattern. Thus, the stitch patterns may refer to the pattern of discrete attachment sites between the two layers.

Embodiments of the present disclosure may include stitch patterns wherein the pattern may be comprised of a plurality of straight lines oriented along one or more axes of the material. In some embodiments, a subset of straight lines oriented along different axes of the material may intersect at least a portion of the plurality of straight lines, which may form a grid pattern. The stitch pattern may comprise a variety of designs and patterns. Some embodiments may solely include a plurality of parallel lines. Some embodiments may include a stitch pattern comprising a plurality of lines arranged in a zig-zag pattern. Other embodiments may include a stitch pattern with discrete regions which have different patterns.

Embodiments of the present disclosure which include a stitch pattern having a subset of the lines in a zig-zag design may comprise a different amplitude, frequency, or amplitude and frequency relative to another subset of the lines in a zig-zag in the stitch pattern.

Some embodiments may include a stitch pattern having a plurality of lines arranged in a pattern comprising a plurality of curves. Some embodiments may include a wave pattern such as a sinusoidal wave, or an oscillating line pattern. A subset of the lines in a curve pattern may comprise a different amplitude, frequency, or amplitude and frequency relative to another subset of the lines in a curve in the stitch pattern. Some embodiments may include the stitch pattern being continuous, while others may include breaks or interruptions at one or more locations along the pattern. The stitch pattern may comprise a corner-lock stitch pattern.

Some embodiments of the present disclosure may include a stitch pattern which may be comprised of a filament, such as thread, yarn, or the like. In one embodiment, the stitch pattern may comprise a single filament. In one embodiment, the stitch pattern may comprise an upper filament and a lower filament. The upper filament may include a larger diameter relative to the lower filament may comprise substantially the same diameter relative to the lower filament, or may comprise a smaller diameter relative to the lower filament.

The upper filament and the lower filament may include any one or more of chitosan, hyaluronic acid, icodextrin, fibrin, poly(L-lactide-co-D,L-lactide)/polylactic acid, polytetrafluoroethylene, or oxidized regenerated cellulose, including any blended combination thereof or polymerization thereof.

In general, the attachment between the first layer and the second layer may be configured to flexibly attach the two layers so that the combination of the two layers does not change the compliance more than a nominal (e.g., 10% or less) amount. This flexible attachment configuration may be achieved, at least in part, by including regions between the discrete attachment sites that are not attached, so that the first layer and second layer may move, or slide relative to each other as the material is bent, pulled, or manipulated.

The density of the discrete attachment sites may be uniform or non-uniform. As mentioned above, in some embodiments the discrete attachment sites may be distributed in a pattern such as a grid, or overlapping grids. In some embodiments, the density of attachment sites may be relatively low. For example, the density of attachment sites may be less than about 10 attachments/mm$^2$.

In embodiments of the present disclosure wherein the second layer is attached onto the first layer, the second layer may comprise one or more sheets of anti-adhesion layer material, such as ECM, silicone, polyurethane or polylactic acid (PLA). In some embodiments, the attachment of the second layer with the stitching pattern described herein may provide for the one or more sheets of anti-adhesion layer material to be movable relative to the substrate. For example, the one or more sheets may be joined to the first layer with a stitch pattern comprising at least one filament. The filament material may be formed of any appropriate material, including a polymeric material. In some embodiments, the filament material may be formed of the same material as the anti-adhesion layer sheets.

In some embodiments, the attachment stitch pattern securing the first layer to the second layer may comprise a plurality of stitch islands, whereby the at least one filament may be disposed at discrete locations about the material. In some embodiments, that tissue scaffold material may include regions that are unattached (e.g., having no stitch pattern or filament) in between stitch islands. Some embodiments may include a stitched attachment pattern having a plurality of straight lines oriented along one or more axes of the substrate.

In some embodiments, a subset of straight lines oriented along different axes of the substrate may intersect at least a portion of the plurality of straight lines, and thereby may form a grid pattern on at least a portion of the material. The stitch pattern may comprise a variety of designs and patterns. Some embodiments may solely include a plurality of parallel lines. Some embodiments may include a stitch pattern comprising a plurality of lines arranged in a zig-zag pattern. Other embodiments may include a stitch pattern with discrete regions which have different patterns.

Embodiments of the present disclosure which include a stitch pattern having a subset of the lines in a zig-zag design may comprise a different amplitude, frequency, or amplitude and frequency relative to another subset of the lines in a zig-zag in the stitch pattern.

Some embodiments may include a stitch pattern having a plurality of lines arranged in a pattern comprising a plurality of curves. Some embodiments may include a wave pattern such as a sinusoidal wave, or an oscillating line pattern. A subset of the lines in a curve pattern may comprise a different amplitude, frequency, or amplitude and frequency relative to another subset of the lines in a curve in the stitch pattern. Some embodiments may include the stitch pattern being continuous, while others may include breaks or interruptions at one or more locations along the pattern. The stitch pattern may comprise a corner-lock stitch pattern.

Some embodiments of the present disclosure may include a stitch pattern which may be comprised of a filament, such as thread, yarn, or the like. In one embodiment, the stitch pattern may comprise a single filament. In one embodiment, the stitch pattern may comprise an upper filament and a lower filament. The upper filament may include a larger diameter relative to the lower filament may comprise substantially the same diameter relative to the lower filament or may comprise a smaller diameter relative to the lower filament.

The upper filament and the lower filament may include any one or more of chitosan, hyaluronic acid, icodextrin, fibrin, poly(L-lactide-co-D,L-lactide)/polylactic acid, polytetrafluoroethylene, or oxidized regenerated cellulose, including any blended combination thereof or polymerization thereof.

In some embodiments, the one or more anti-adhesion layer sheets may comprise any one or more of chitosan, hyaluronic acid, icodextrin, fibrin, poly(L-lactide-co-D,L-lactide)/polylactic acid, polytetrafluoroethylene, or oxidized regenerated cellulose, including any combination or polymerization thereof.

The above disclosure provides a material primarily comprised of attaching an anti-adhesion layer to a tissue scaffold, but the above disclosure may also be applied to attaching a tissue scaffold to a microstructured surface. In some embodiments, all three parts (first layer, second layer, and microstructured surface) may be provided concurrently in one attachment procedure. In some embodiments, the microstructured surface may also be incorporated onto any layer as disclosed herein. Though the disclosure may provide for a microstructure layer, the layer may be integral with or incorporated into another layer.

Embodiments of the present disclosure may include a microstructured surface attached or integrated into the tissue scaffold material. In some embodiments, the tissue scaffold material may be comprised of three layers including a first layer, a second layer, and a microstructured layer. The microstructured layer may be configured to provide the material with the ability to maintain positionability and/or fixation to a surface.

An intersurface adherence may be formed between two surfaces when an interface volume disposed between the two surfaces includes both high surface tension and low surface tension substances. This intersurface adherence may be caused by a Wenzel-Cassie interface, which when formed is suctional. The suctional aspect results when the constituents of the interface volume are organized such that the liquid interface maximally contacts a microstructured surface. In a sense, the interface volume may diffuse into the microstructure, where it then becomes pinned and produces the adherence effect or force.

While the pinning force in any microscopic area of the interface may be small, the pinning force over a macroscopic area may be unexpectedly large.

Intersurface adherence may take many forms, but generally originates due to the interaction of a spatially varying surface energy of a microstructured surface and the surface energies of various liquids and solids present on the contact surface. Frequently, combinations of types of intersurface adherence occur in practical situations. For example, a condition known as "stick-slip" may be associated with the formation of Schallamach waves. The phenomenon of stick-slip minimizes destructive interaction between surfaces undergoing relative displacement. Stick-slip may be characterized by temporally distributed intervals of interfacial states comprising alternating conditions of near zero adherence and near infinite adherence.

Stick-slip may rely on the difference between shear force and peel force. When a target substrate is put under enough compressional force it may buckle creating an orthogonal displacement which may then access the peel mode of dehesion. Dehesion may cause a lateral translation (slip) which may remove the orthogonal displacement and the shear force is re-established. This phenomenon may be responsible for some of the repositional aspects of the present embodiments disclosed herein.

For example, in some embodiments, a microstructured surface may be designed with Schallamach waves which may include the design feature where orthogonal displacements of a target surface do not change the interfacial distance or volume, consequently not generating a peel force and prevents the slip phenomenon. In embodiments, in which the target surface may be undergoing compressional waves from external sources, a periodic distribution of gripping surfaces may be able to transmit the compressional waves without causing the relationship between the microstructured surface and the target surface to be altered.

In some embodiments, the microfeatures on a microstructured surface may be ordered, usually periodically, and on many "stacked" levels. When microstructures are periodically formed on several size scales they may be said to be hierarchical, and may have a fractal dimension greater than 2.

Referring to FIG. 1, a microstructured surface 100 may include a branching ratio with may be defined by three hierarchical microfeatures 102, 104, 106. In some embodiments, the first microfeatures 102 may be spaced 1000 microns apart center-to-center (pitch), the second microfeatures 104 may be spaced 100 microns apart, and third microfeatures 106 may be spaced 10 microns apart. The third microfeatures 106 may be disposed on the top surface 108 of the second microfeatures 104. The second microfeatures 104 may be disposed on the top surface 110 of the first microfeatures 102. Thus, a line 112 may define a branching ratio where length 114 may be 10 times the length 116, and wherein length 116 maybe 10 times the length 118. The line 112 may define a fractal dimension of 2.1=2+ratio of successive lengths, where 2 is the dimension of the surface with no microstructure.

Figure 2A:
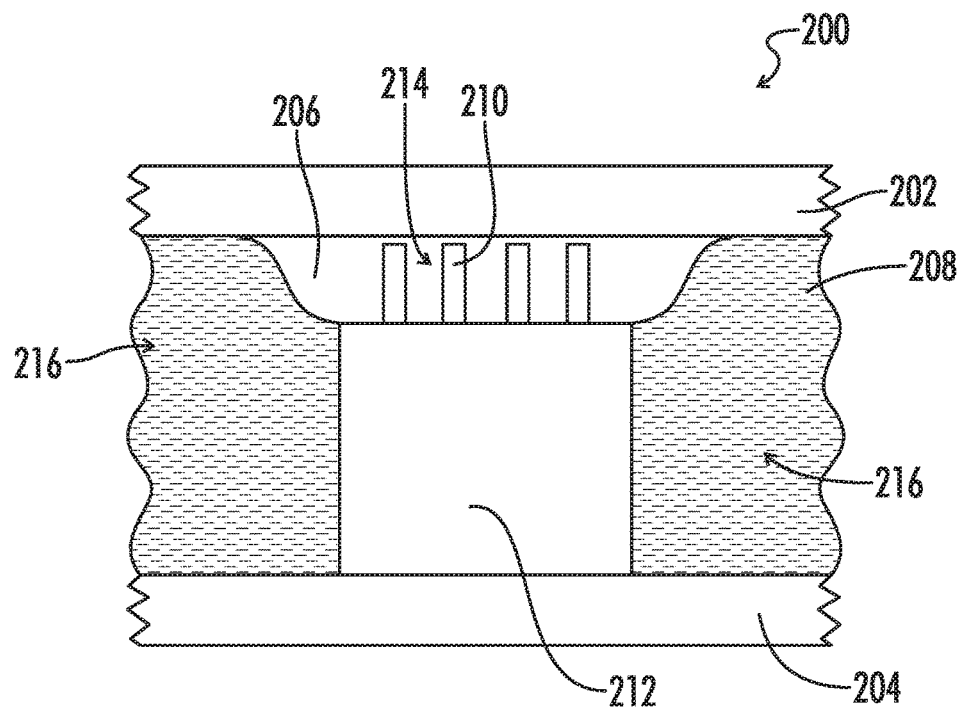
FIG. 2A is an illustration of one embodiment of a Wenzel-Cassie interface between a target surface and a microstructured surface.
Figure 2B:
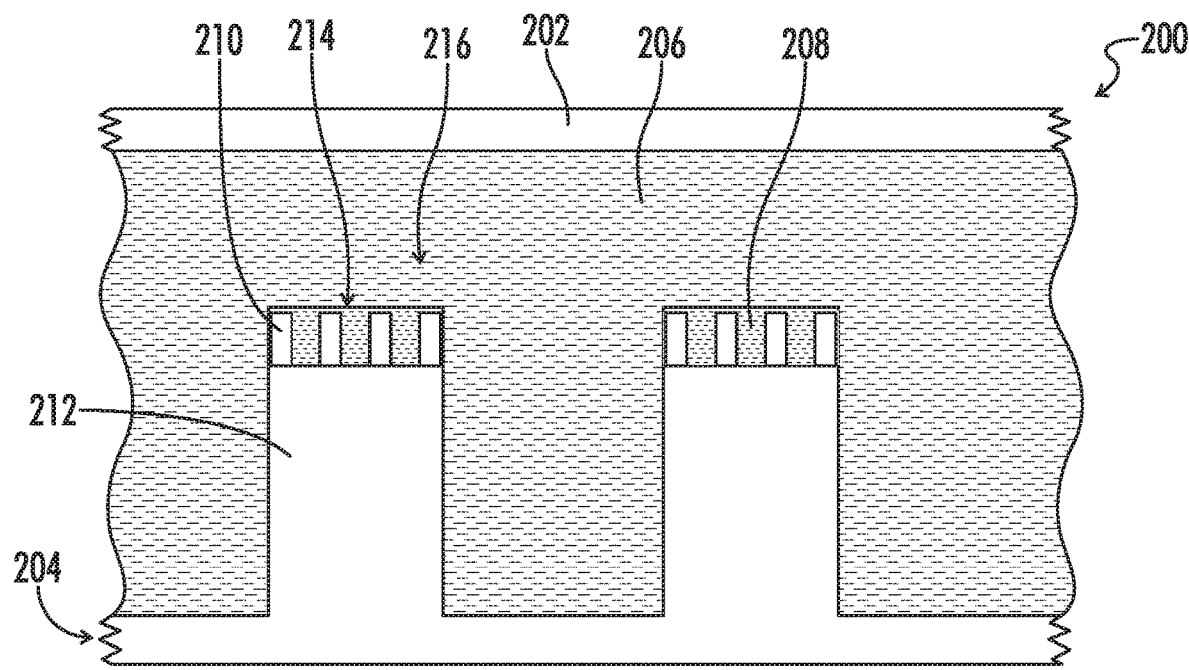
FIG. 2B is an illustration of another embodiment of a Wenzel-Cassie interface between a target surface and a microstructured surface.

In some embodiments, the minimal surface energy fluid may be a gas which has zero surface energy. Referring to FIGS. 2A and 2B, a Wenzel-Cassie interface 200 may be formed between a contact surface 202 and a microstructured surface 204. The interface 200 may be comprised of a first liquid 206 and a second liquid 208. In some embodiments, the microstructured surface 204 may cause the interface 200, which may normally be homogeneous in the first and second liquids 206, 208, to organize around hierarchical microstructures 210, 212. The organization may cause segregation of the fluids 206, 208 into spatially localized domains 214, 216. The total energy of the system may decrease due to this organization, which may create an adherent force. The energy required to disrupt a Wenzel-Cassie interface may be approximately equal to the energy needed to return the interface 200 to the homogeneous state.

Embodiments of the present disclosure may include a first layer, second layer, and third layer, wherein the second and third layers are attached to the first layer. In some embodiments, the first layer is attached to the second layer on a first side of the first layer, and the first layer is attached to the third layer on a second side of the first layer. In some embodiments, the first layer may comprise a tissue scaffold material. The second layer may comprise an anti-adhesion composition. The third layer may comprise a microstructure surface. In some embodiments, the third layer may be combined with the first or second layer such that the microstructure surface is integral with the first or second layer.

In some embodiments, the third layer may comprise a hierarchical microstructure wherein a first microfeature has a second microfeature thereon. In some embodiments, a third microfeature may be disposed about the second microfeature. This continued "stacking" of microfeatures may include additional microfeatures disposed about the previous microfeature. In some embodiments, the third layer comprising a microstructure surface may be configured to provide an adherence effect such that the combined layers may be temporarily adhered to a target surface. In some embodiments, the third layer may include a microstructure surface that provides a fixation effect such that the combined layers may be fixated to a target surface for a more permanent time period otherwise unsupported against the target tissue and in the absence of setting or curing agent.

Methods for making embodiments of the disclosed materials are also described herein. Methods may comprise, for example, attaching an anti-adhesion layer material via one or more stitched attachment patterns to secure the anti-adhesion material to a scaffold material described or exemplified herein. In some embodiments, such methods may include weaving or sewing a filament material such that one or more sheets comprising an anti-adhesion layer material may be attached to a scaffold material described or exemplified herein. In some embodiments, the scaffold may include a first pattern woven, sewn, or embroidered onto it utilizing a filament material having a greater bioabsorbability than the scaffold material. For example, in some embodiments, the mesh may have a high compliance property in its native state but may have a compliance-limiting stitching pattern woven, sewn, or embroidered onto it utilizing a lower compliance filament material. The mesh may then be attached to an anti-adhesive layer via an attachment pattern of discrete attachment sites (e.g., stitches).

It will be understood by those skilled in the art that the embodiments of the present disclosure may be of beneficial use to repair tissue. For example, disclosed herein are methods for inhibiting adhesions and positioning the material and fixing the material as an implant, all aspects of which are understood to be central in repairing or reconstructing tissue in a subject in need thereof. Such methods may generally comprise implanting an implant or scaffold material comprising an anti-adhesion layer and a positioning/fixation layer wherein the positioning/fixation layer may be sewn or embroidered into the implant or scaffold material. In some embodiments, the implant or scaffold material may include one or more anti-adhesion layers sewn onto the implant or scaffold at a location in the body of the subject in need of tissue repair or tissue reconstruction.

As used herein, "tissue" may be any tissue in the body, including soft tissue. In some methods, the tissue may comprise a hernia, such that the implant or soft tissue repair graft is used to repair the herniation. Once implanted, the anti-adhesion layer may inhibit adhesions between tissue in the body and the implant or scaffold and may also further inhibit adhesions between adjacent tissues in the body that are proximal to the implant. It will be understood that fixation of the implant includes maintaining a positional association between the soft tissue defect and the scaffold. In some embodiments, the fixation portion may communicate a restraining force to the scaffold prior to tissue in-growth into the scaffold. In some embodiments, the fixation portion may continue to play a supporting role even after the scaffold is fully integrated into the body. It will be understood that the use of the term "subject" may include a human being or other animal (e.g., veterinary animal, non-human animal, etc.).

Some embodiments of the present disclosure may include a hernia repair graft. In some embodiments, the hernia repair graft may be comprised of a first layer comprising a tissue scaffold layer, a second layer comprising an anti-adhesion layer, and a third layer for positioning or affixing the graft to tissue, wherein the second and third layer are flexibly attached to the first layer with a pattern of discrete attachment sites. In some embodiments, the pattern of discrete attachment sites may alter the compliance of the stacked first, second and third layers by less than 10% and adjacent regions of the first layer, second layer and third layer between the discrete attachment sites may slide relative to each other.

In some embodiments, a hernia repair graft may include a first layer comprising a knitted, non-bioabsorbable mesh and a first pattern embroidered into the mesh with a bioabsorbable material. The hernia repair graft may further include a second layer comprising at lease one sheet of anti-adhesion material attached at discrete attachment sites along the first layer such that adjacent discrete attachment sites may be separated by a distance of between 1 mm and 20 mm. The hernia repair graft may further include a third layer comprising at least one sheet of microstructured material attached at discrete attachment sites along the first layer such that adjacent discrete attachment sites may be separated by a distance of between 0.1 mm and 10 mm, and adjacent regions of the first layer, second layer and third layer between the discrete attachment sites may slide relative to each other.

In some embodiments of the present disclosure, a hernia repair graft may include a first layer attached to a second layer and the third layer attached on the first layer. The second layer may include an anti-adhesion layer formed of an absorbable material and a first pattern stitched into the second layer with a bioabsorbable material. The first layer may include a scaffold material comprising a plurality of sheets of extracellular matrix material (ECM). And the third layer may include a positional/fixation material comprising hierarchical microstructures for positioning the material, and tissue penetrating barbs for fixing the material. The third layer may have at least a portion comprised of polypropylene. The second and third layers may be flexibly attached to the first layer with a second pattern of discrete stitched attachment sites, wherein the second pattern of discrete stitched attachment sites is less dense than the first pattern stitched into the anti-adhesion sheet. In some embodiments, adjacent discrete attachment sites may be separated by a distance of between 1 mm and 20 mm. The hernia repair graft may further include a third layer comprising at least one sheet of microstructured material attached at discrete attachment sites along the first layer such that adjacent discrete attachment sites may be separated by a distance of between 0.1 mm and 10 mm, and adjacent regions of the first layer, second layer and third layer between the discrete attachment sites may slide relative to each other.

In any of the graft embodiments disclosed herein, the first pattern (e.g., the reinforcing pattern) may be applied to the third layer, where the third pattern (e.g., the attachment pattern) may be a third stitching pattern of discrete attachment sites. The third pattern may be less dense than the first pattern in the plane of the third layer.

In general, the tissue scaffold may be comprised of a mesh. The mesh may be a knitted mesh, a woven mesh, or a formed mesh. The mesh may be formed of polypropylene, polytetrafluoroethylene (PTFE), nylon, polyester, or the like, including combinations thereof. The mesh may have an open cell pore diameter of between 1 mm and 10 mm. The mesh may be formed of a warp knitted filament having a diameter of between 1 micron and 250 microns. For example, the mesh may be formed of a warp knitted filament having a diameter of between 3 microns and 100 microns. The mesh may be formed of a plurality of fibers that are knitted together (multi-filament) or a monofilament. In some variations multi-filament fibers (for either or both the mesh and the sewn materials) may be preferred because they may be stronger.

In general, the positional/fixation layer may include a polymeric sheet with fenestrations to allow tissue growth from the tissue surface to the scaffold layer. The positional portion of the layer may include a microstructured surface. The microstructures may be arranged hierarchically, with a fractal dimension greater than 2. Generally, the higher the fractal dimension, the greater the positional strength. The positional portion of the layer may provide for localization of the implant to the tissue, which facilitates surgical placement, especially laparoscopically.

Figure 3A:
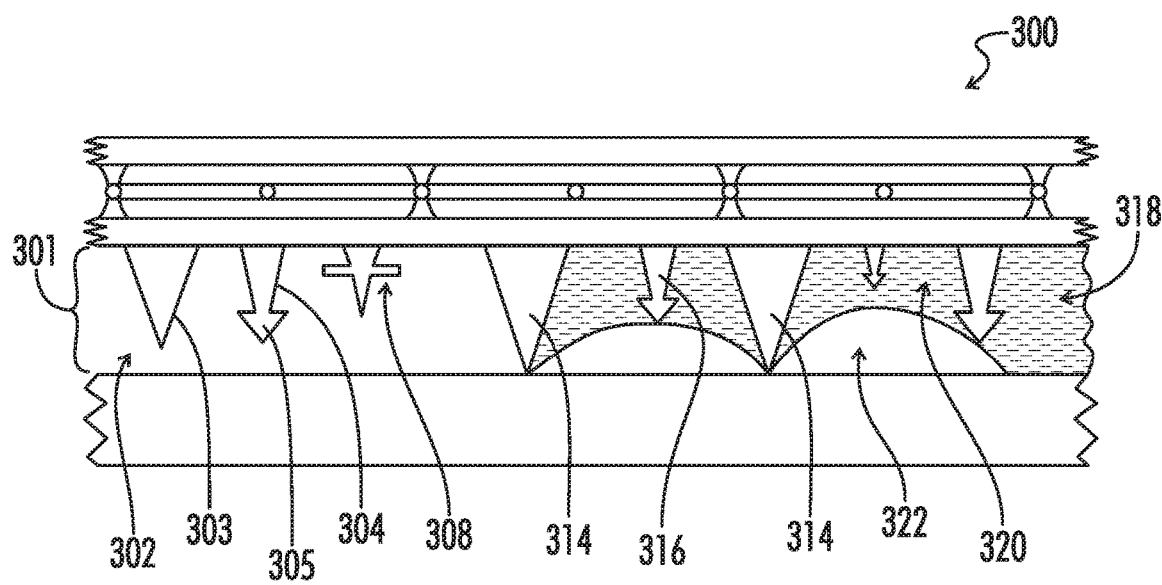
FIGS. 3A and 3B are illustrations of an embodiment of the present disclosure with an interface volume between a target surface and microstructure.

In some embodiments, the third layer may comprise a fixational aspect which may invasively engage a contact surface. Referring now to FIG. 3A, a soft tissue graft 300 is illustrated. The soft tissue graft may include a positional/fixation layer 301. In some embodiments, a tissue engaging structure 302 may be a tapered pillar 303. In some embodiments, a tissue engagement structure 302 may be a barbed microfeature 304. The barb 305 may be utilized to invasively engage the target surface 312, however the engagement of the barb may reduce the repositionability of the soft tissue graft 300. Thus, the positional/fixation layer 301 may be configured such that the barbed microfeature 304 is positioned at a greater distance 306 from the target surface 312 in relation to another barbed microfeature 304. A plurality of barbed microfeatures 304 may be configured such that the various subsets of the plurality of barbed microfeatures have increasing distances from the target surface 312. Such a configuration with a variety of distances from the target surface 312 may allow for an increasing number of barbs 305 to engage the target surface as a function of time. In some embodiments, a tissue engaging structure 302 may include a microstructure ring 308. The microstructure ring 308 may limit the depth of invasive engagement of the tissue engaging structure 302 with the target tissue 312. In some embodiments, the microstructure ring 308 may be configured such that the ring provides a weak stop, which can be overcome by the application of additional pressure by the clinician, thus providing greater fixation of the soft tissue graft 300 to the target surface 312 at a desired time.

In some embodiments, the positional force may be provided by microstructures 314 and 316 and interfacial volume 318 comprising at least two fluids 320 and 322.

In some embodiments, the positional-fixation layer may be fenestrated. The fenestrations may be any size practical to the size of the soft tissue repair graft 300. An important consideration is that the positional and fixational strengths of the soft tissue graft 300 are proportional to the surface area of the microstructured surface 301. Accordingly, the larger the areal ratio the larger the positional and fixational strengths for a given fractal dimension and barb density.

For surgical procedures and associated implants where the center of the implant is positioned first, and the remainder of the implant is arranged to accommodate this initial position, the areal ratio may decrease radially from the center of the implant.

For surgical procedures and associated implants where the perimeter of the implant is positioned first, the areal ratio may be greatest near the perimeter. The areal ratio may be discretized into high areal ratio localized regions, which can mimic conventional tacking and/or suturing procedures. In some embodiments, some regions may be populated by barbs alone, and in other regions may be populated by barbless microstructures alone.

In some embodiments of the present disclosure, the distribution of the positional structures (microstructure) and the fixation structures (barbs) may be different within a soft tissue graft, or medical implant generally. Similarly, in some embodiments the barb position and density along tissue engaging features may vary across the surface of the positional/fixation layer.

In some embodiments, the positional/fixation layer may further be comprised of a substrate surface to which the microstructures and/or tissue engaging structures are disposed upon. In some embodiments, the microstructures and/or tissue engaging structures are integral with the substrate surface, and therefore they may be composed of the same material/composition. In some embodiments, the microstructures and/or tissue engaging structures may be disposed about the substrate surface and are composed of a different material than the substrate surface. In one embodiment, the microstructures and/or tissue engaging structures may be embossed on the material of the substrate. In some embodiments, the tissue engaging structures may include metallic or hard plastic barbs applied at select locations on the embossed substrate.

Figure 3B:
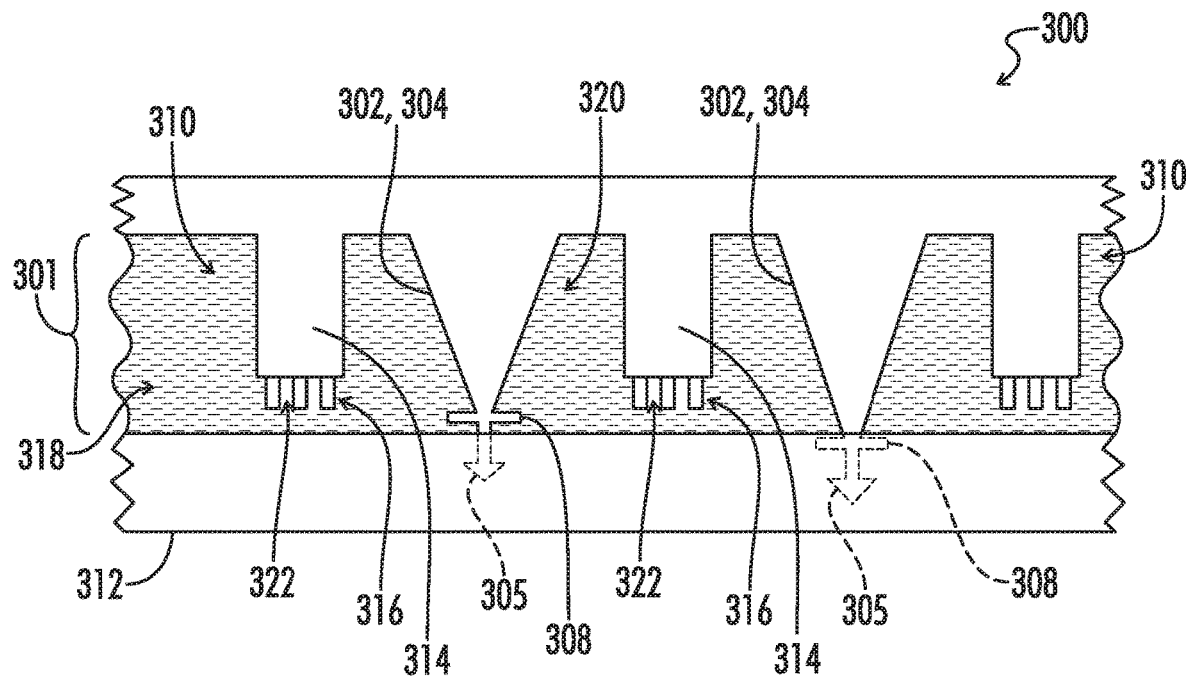

Referring now to FIG. 3B, the positional/fixation layer 301 may include a hierarchical microstructure 310. The hierarchical microstructure may include a first microfeature 314 and a second microfeature 316, wherein the second microfeature is disposed about the first microfeature. In some embodiments, the first microfeature may have a dimension(s) that is larger than the second microfeature. In some embodiments, the positional/fixation layer may include tissue engaging structures 302. The tissue engaging structures 302 may include a barbed end 305 with a microstructure ring 308 disposed about the tapered pillar. As disclosed previously, the microstructure ring 308 may act as a weak stop to initially prevent further insertion of the tissue engaging structure 302 into the target surface 3012. With additional pressure or force, the microstructure ring 308 may be inserted into the target surface 312. In some embodiments, the positional force may be provided by hierarchical microstructures 314, 316 and interfacial volume 318 comprising at least two fluids 320, 322. In some embodiments, the fixation force may be provided by tissue engaging structure 302. The soft tissue graft 300 may be initially placed about the target surface 312 and the initial positionability of the soft tissue graft may be maintained by the hierarchical microstructures 310. Once the position of the soft tissue graft 300 is acceptable to the clinician, or within certain requirements/parameters, the soft tissue graft may be fixated in position by applying pressure to the graft and thereby engaging the tissue engaging structures 302 into the target surface 312.

Figure 4:
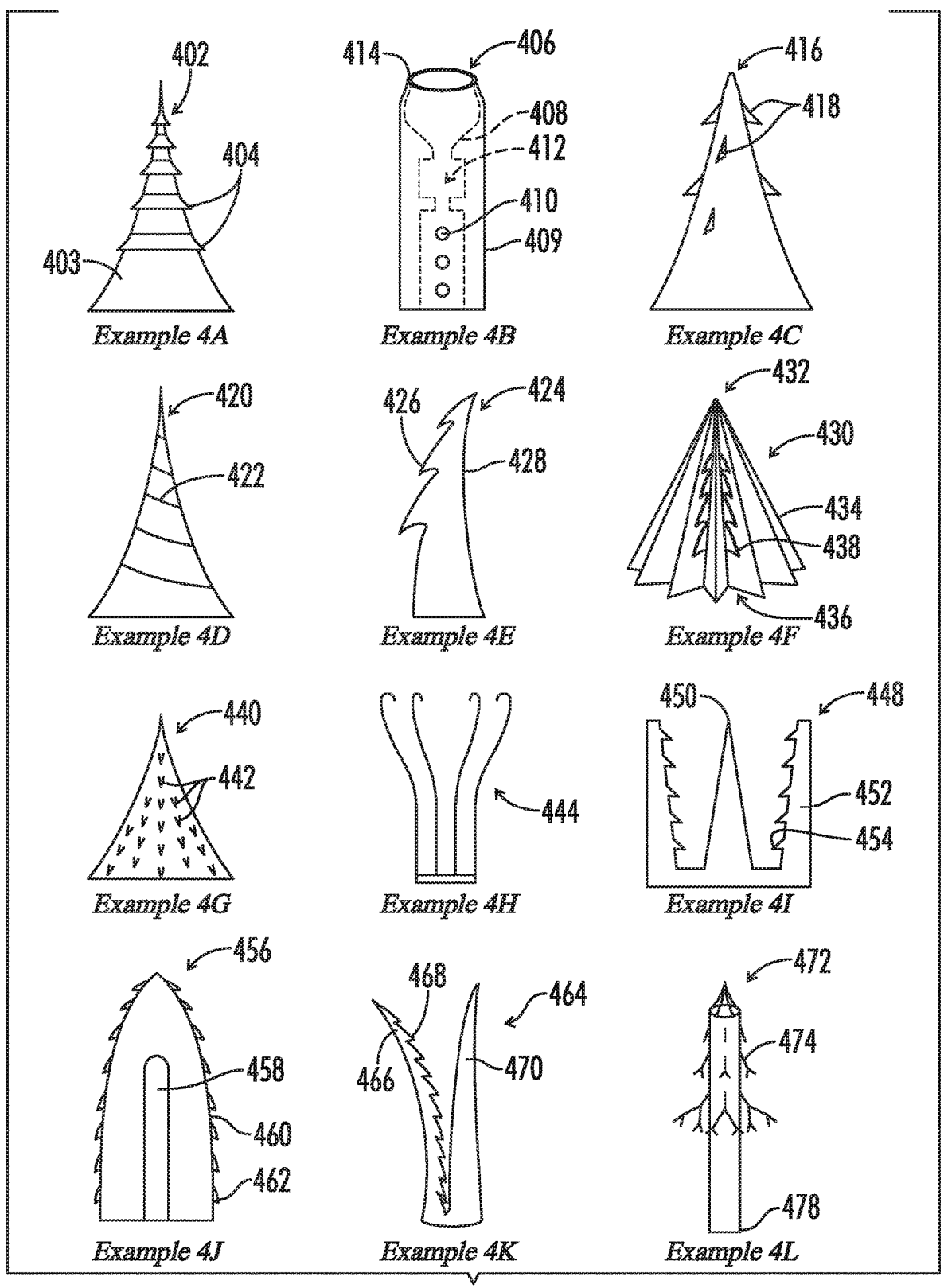
FIG. 4 depicts various embodiments of microstructure geometries.

Referring now to FIG. 4, various examples of tissue engaging structures 400 with barb designs are given. Example 4A includes a conical structure 402 with a circular cross section. The surface 403 may be disposed with circularly enwrapping recurved, protruding barbs 404. Example 4B includes a hollow cylinder 406 with engaging inner structure 408. The outer surface 409 of the hollow cylinder 406 may include at least one hole 410 which may allow fluid trapped in the interior 412 to be expelled so that tissue can pass into the interior. A cutting surface 414 may allow tissue to easily pass into the interior 412. Example 4C includes a conical structure 416 with a circular cross section. Discrete barb projections 418 are distributed axially. Adjacent barbs may be offset from one another along the height of the structure. Example 4D includes a conical structure 420 with a circular cross section. A continuous barb projection 422 may be disposed helically around the surface of the structure. Example 4E includes a blade-like cross section 424. The cross-section 424 may be recurved, with one side having discrete barb projections 426 disposed thereon, and the opposing side including a cutting surface 428. Example 4F includes conical structure 430 with a fluted surface 434 conical structure with cutting point 432. The valleys 436 of the flutes may include barb projections 438. Example 4G includes a conical structure 440 with a circular cross section. The surface of the conical structure 440 may include flexible barb projections 442 disposed thereon. Flexible barb projections 442 may include a curved outline in some embodiments. Example 4H includes a circular arrangement of flexible fibers 444, which may spread radially when pressed on a surface. Example 4I includes a hollow, cylindrical structure 448 with central solid conical structure 450 having a circular cross section. The structure 448 may include an outer wall 452 which may include barb projections 454 disposed on the interior portion of the outer wall. Example 4J includes a blade-like structure 456 with concave axial flute 458. The structure 456 may include a cutting edge 460 of with barb projections 462 disposed thereon. Example 4K includes a structure 464 comprising two prongs. A first prong 466 may have a blade-like, recurved structure. It may further include barb projections 468 disposed thereon. A second prong 470 may include a tapered cylindrical pinning structure. Example 4L includes a needle-like structure 472 having stiff fiber-like barb projections 474 disposed thereon. The barb projections 474 may bifurcate with the bifurcation nodes increasing per barb toward the base 478 of structure 472.

The presently disclosed subject-matter is further illustrated by the following specific but non-limiting examples. The following examples may include compilations of data that are representative of data gathered at various times during the course of development and experimentation to the presently disclosed subject matter. The following examples are meant to be illustrating and are not exhaustive or limiting.

Example 1

A Soft Tissue Repair Graft Using Wenzel-Cassie Fixation

Figure 5:
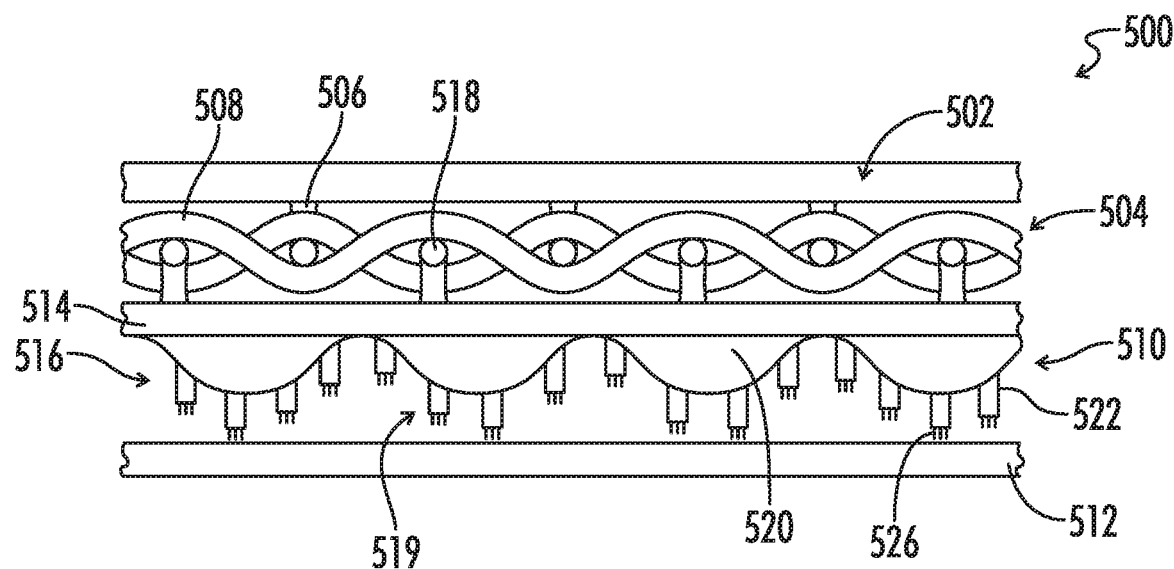
FIG. 5 is an illustration of an embodiment of a Wenzel-Cassie soft tissue repair device.

Referring to FIG. 5, a soft tissue repair graft 500 is illustrated. In some embodiments, the soft tissue repair graft 500 may include an anti-adhesion layer 502, which may be comprised of an absorbable layer having a thickness of between 5 and 1000 microns. The absorbable layer may be composed of biocompatible materials such as polylactic acid, polycaprolactone, polyester urethane, and the like. The soft tissue repair graft may further comprise a tissue scaffold layer 504 which may be attached to the anti-adhesion layer 502 via linking sites 506. The linking sites 506 may be continuous or discrete. In some embodiments, the linking sites 506 may be comprised of an adhesive. In some embodiments, the linking sites may be comprised of a solution of the polymer comprising the anti-adhesion layer 502 and cured around the strands 508 of tissue scaffold layer 504. The tissue scaffold layer 504 may be continuous or woven, such as a mesh as depicted in FIG. 5. In some embodiments, the strands 508 of the tissue scaffold layer 504 may include at least a portion of the strands' surface coated and distinct from linking sites 506. In some embodiments, the tissue scaffold layer 504 may comprise a nonabsorbable material such as polypropylene, polyester, polyurethane, or the like. In some embodiments, the tissue scaffold layer 504 may include absorbable materials. In some embodiments, the soft tissue graft 500 may include a microstructure layer 510 that may be repositionable on a target surface 512 without target surface damage. In some embodiments, the target surface 512 may be living tissue. The microstructure layer 510 may comprise discrete islands or it may be a continuous layer. The microstructure layer 510 may comprise a substrate layer 514 upon which the microfeatures 516 may be disposed. In some embodiments, the microfeatures 516 may be formed directly on the tissue scaffold layer 504. The microstructure layer 510 may be attached to the tissue scaffold layer 504 through distinct links 518 or utilizing the same links 506 as disclosed in attaching the anti-adhesion layer 502 to tissue scaffold layer 504.

In some embodiments, the microfeature 516 may be comprised of a hierarchical microstructure 519. For example, in some embodiments the hierarchical microstructure may include a first microstructure being a sinusoid pattern 520. The sinusoid pattern 520 may have an amplitude in a range of 100 to 1000 microns. Additionally, the sinusoid pattern 520 may have a pitch within a range of 100 to 1000 microns. In some embodiments, a second microstructure in the form of pillars 522 may have a diameter in the range of 10 to 100 microns, a pitch in the range of 10 to 100 microns, and a height in the range of 10 to 300 microns. The second microstructure may be disposed about the first microstructure. In some embodiments, the second microstructure pillar 522 may include a cross section being circular, square triangular, rectangular, or any other polygon shape. In some embodiments, a third microstructure may be disposed about the second microstructures 526. The third microstructures 526 may be smooth or designed, as in FIG. 4, to engage invasively target surface 512. Various degrees of target surface localization may be achieved by varying the degree of target surface penetration, including no penetration, without compromising the Wenzel-Cassie type of positionability.

In some embodiments, the microstructure layer 510 may be comprised of one material as already listed previously in this disclosure. In some embodiments the microstructure layer 510 may be comprised of any appropriate implantable and/or biocompatible material, including metals, and higher durometer materials, such as PET. Embodiments which may comprise a substrate portion 514 may include the substrate portion to be of an elastomeric (low durometer) material. In some embodiments, the microstructures 516 disposed on the substrate portion 514 may be of a high durometer material. This combination of substrate portion 514 and microstructure 516 may make the microstructure layer 510 maximally conformable to the target surface 512.

It should be understood, while the examples presented here are directed to particular aspects of repairing soft living tissue, the embodiments of this disclosure may be adapted to any application where a defect in a target surface is to be strengthened and/or supported.

By way of example, the following microstructures were deployed on a soft tissue graft of the present disclosure.

TABLE 1

| | Shape | Array | Width | Pitch | Height |
|---|---|---|---|---|---|
| Layer 1 | Sinusoid | Triangular | 750 μm | 750 μm | 220 μm |
| Layer 2 | Fluted Circle | Triangular | 35 μm | 45 μm | 45 μm |
| Layer 3 | Circle | Triangular | 3 μm | 6 μm | 4 μm |

This soft tissue graft when placed on animal tissue resisted displacement under 258+/−17 grams shear force per square centimeter of surface contact.

Example 2

Hernia repair device with repositionable, flexible localization.

Figure 6:
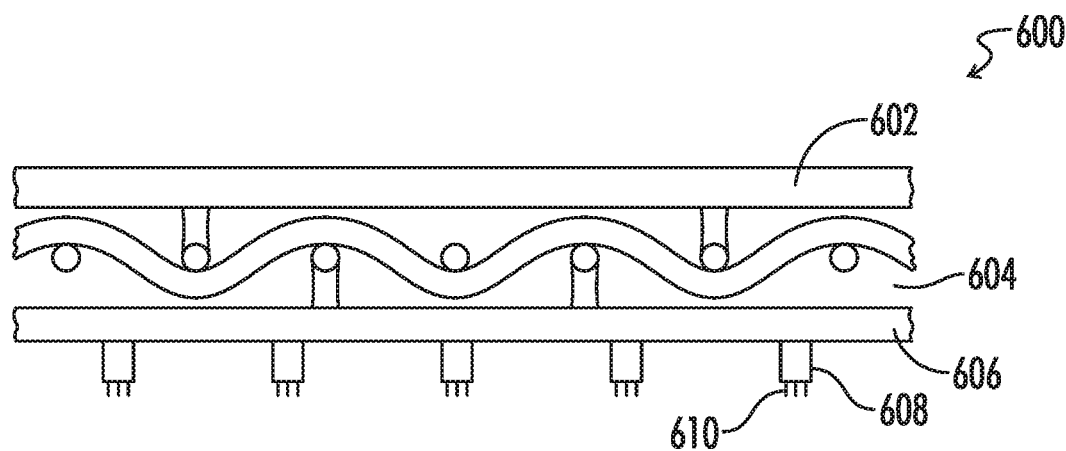
FIG. 6 is an illustration of an embodiment of a Wenzel-Cassie soft tissue repair device with flexible layers.

Referring now to FIG. 6, a soft tissue repair device is illustrated. The soft tissue repair device 600 may include an anti-adhesion layer 602 comprising polylactic acid, a tissue scaffold layer 604 comprising polypropylene mesh coated with polyurethane, and a third microstructure layer 606 comprising microstructured polylactic acid. The microstructure layer 606 may be comprised of hierarchical microfeatures including first circular pillars 608 having a diameter in the range of 10 to 100 microns, pitch in the range 10 to 100 microns, and height in the range of 30 to 120 microns, and second circular pillars 610 disposed on first pillar 608. The second pillars 610 may have a diameter in the range of 10 to 50 microns, pitch in the range 10 to 50 microns, and height in the range of 30 to 80 microns.

Tests of the embodiment described above for FIG. 6 were performed with and without applied normal force. The applied normal force was 50 g/cm². Tests were performed in shear and normal force (peel).

Shear Force Setup:

Two uniform thickness (about 2 cm) slabs of beef chuck were immersed in water and placed side by side. A composite mesh was placed face down on top of each meat slab with initial hand pressure. No gap was created.

One meat slab was sutured at its corners and once in the middle to a rigid plastic sheet. The other meat slab was sutured at five equi-distant points on its distal edge. The 5 suture lines were drawn together and fixed to a thick cord such that when the cord was pulled the forces in each suture line were approximately equal. The cord was tracked around a pulley to a position of 90 degrees and attached to the head of an Instron. The pulley and meat were aligned so that the tension created on the cord was in the plane of the meat. The meat was kept wet by spritzing liberally with saline. Experimental runs which created torquing of the meat were discarded. Head rate was 5 cm/min. Force per unit area of meat-mesh contact was calculated.

In the normal force arm of the study, another plastic sheet was placed over the top of the meat/mesh combination and weighted uniformly to 50 g/cm².

In the mesh-only arm of the study, the mesh was sutured at 4 places on each meat slab, for a total of 8 sutures. The bite was approximately 1 cm.

Normal Force Setup:

The setup is similar to the Shear Force Setup except a third piece of meat is pulled through the gap between two pieces of meat, one of which is sutured down. The pull force is supplied by suture lines passing through the mesh. No normal force is applied at the gap. Suture: Prolene 5-0.

Study Arm 1: Shear Force without normal force.
Study Arm 2: Shear Force with normal force.
Study Arm 3: Shear Force with suture only
Study Arm 4: Normal force with applied normal force.
Results:

|  | Force per area | Total Force |
|---|---|---|
| Composite Mesh (Shear without Normal Force) | 25.8 +/− 14 cm² | 2.5 kg |
| Composite Mesh (Shear with 50 g/cm² Normal Force) | 350 +/− 198 cm² | 33.6 kg |
| Plain Mesh w/Suture (shear w/o normal force) |  | 51.0 kg |
| Composite Mesh (Normal with 50 g/cm² Normal Force) | 112 +/− 64 cm² | 10.8 kg |
| Composite Mesh (Shear with 11 g/cm² Normal Force)* | 217 +/− 183 cm² | 20.8 kg |

*Normal intra-abdominal pressure
N = 10, Mesh area: 8 cm x 16 cm, Force in grams.

Example 3

Two-Level Soft Tissue Repair Device

In many applications of the present disclosure, it may be desirable to place a device upon a target surface, have the device adhere temporarily, reposition the device to a more desired location, and then activate a more permanent fixation of the device to the target surface. It will be understood that "more permanent" does not indicate a non-reversible fixation, but a longer lasting fixation than the temporary adherence.

Figure 7:
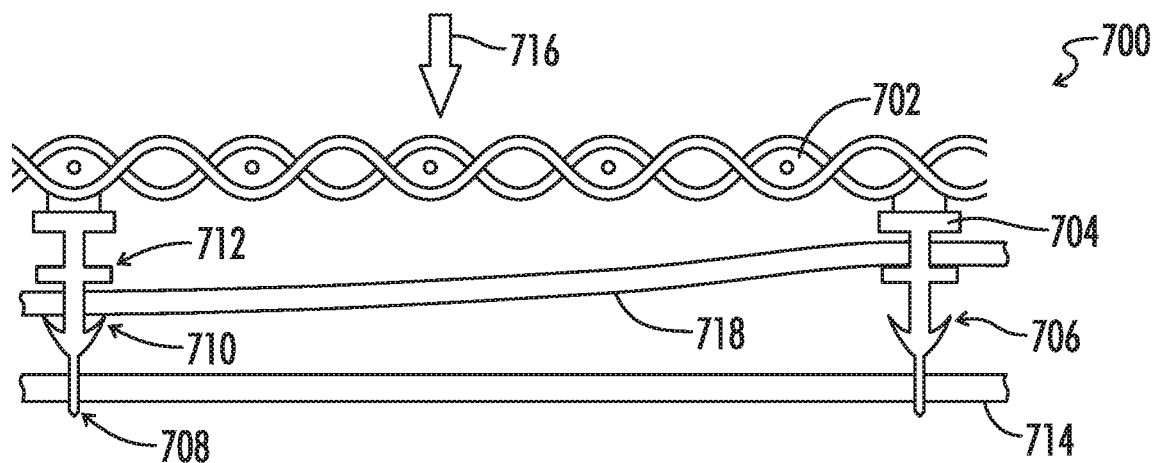
FIG. 7 is an illustration of an embodiment of a two-level soft tissue repair device.

Referring now to FIG. 7, a two-level soft tissue repair device 700 may comprise a polypropylene mesh 702 bonded to a perimeter microstructure layer 704. The perimeter microstructure layer may include a first microstructure 706 comprising a tip portion 708, barbed portion 710, and stop portion 712. When device 700 is positioned on target surface 714 using light pressure, device 700 may invasively engage the target surface wherein only the tip portion 708 engages the target surface. This engagement may provide an adherence of the device 700 to the target surface, but the adherence may allow for the device to be easily repositioned. When additional force is applied to the device 700 in direction 716, the barb 710 may invasively engage the target surface 714 and provide a more permanent fixation such that the device adheres in a non-repositionable position. Stop 712 may be utilized to limit the depth at which barb 710 may be allowed to engage the target surface 714.

Example 4

Wenzel-Cassie Two-Level Soft Tissue Repair Device

Figure 8A:
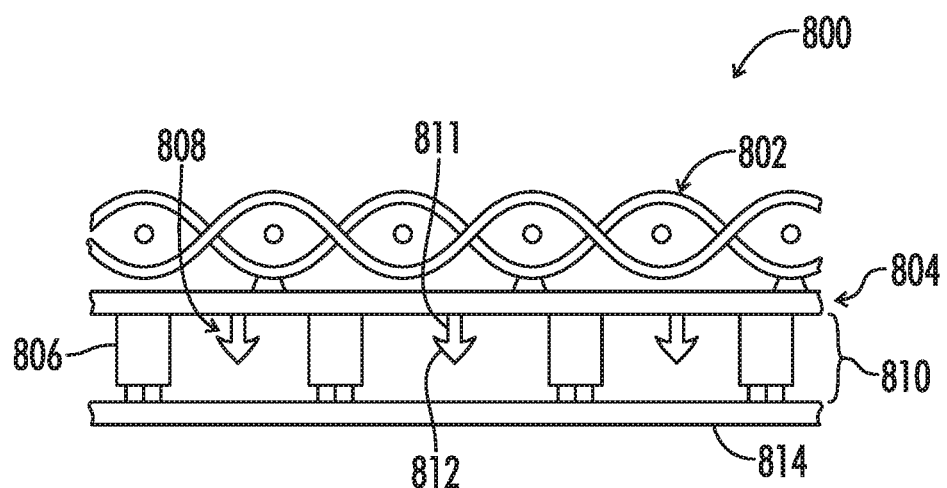
FIGS. 8A and 8B are illustrations of embodiments of a Wenzel-Cassie two-level soft tissue repair device.
Figure 8B:
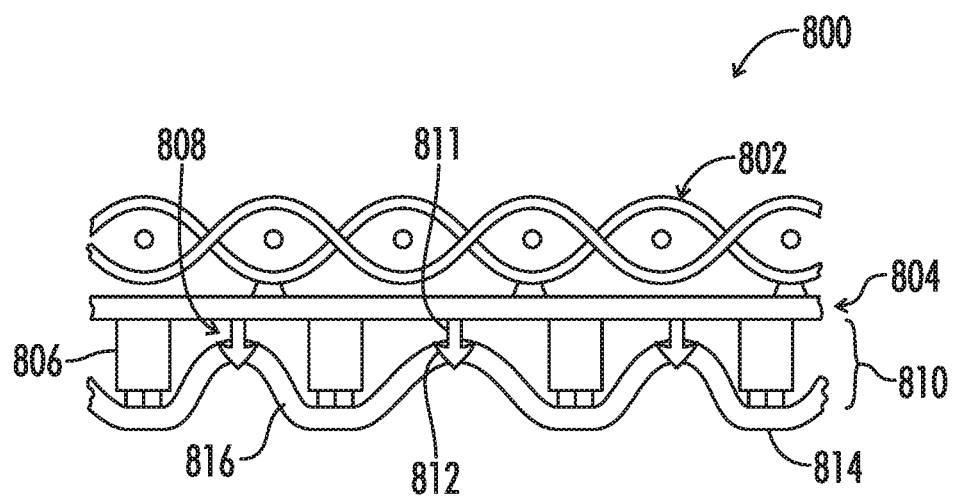

Referring now to FIGS. 8A and 8B, a two-level soft tissue repair device 800 is illustrated. The two-level soft tissue repair device 800 may comprise a polypropylene mesh 802 bonded to a microstructure layer 804 comprising Wenzel-Cassie microstructures 806 and target penetration structures 808. Wenzel-Cassie structures 806 may be comprised of a hierarchical composite pillar 810. Target penetration structure 808 may include a pillar 811 with a barb 812. Under light pressure the target surface 814 (FIG. 8A) may remain in a non-deformed state such as its native state, depicted at position 814. When greater pressure is applied to the device 800, the target surface 814 may be deformed such that the target surface may deform around the Wenzel-Cassie structures 806 and contact the target penetration structure 808, as depicted at position 816 (FIG. 8B). When pressure is released from the device 800, the device and target surface are fixated such that the device will remain in position for a substantial amount of time, on the order or hours, days, and/or weeks.

Example 5

Soft Tissue Device for Grasping

A soft tissue adhesive device comprises the microstructure of Example 2 bonded to an elastomeric rubber sheet. The ability of this device to lift soft tissues, such as meat, fruits, and vegetables was tested by measuring the shear force under 1 g/cm² normal force.

The soft tissue adhesive device was placed on a planar slice of the test article, weighted at 1 g/cm² and pulled in the plane of the test article. All test articles were moistened by dipping in water prior to testing.

Results:

| Test Article | Shear Force (N = 10, g/cm²) | Target Article Failure* |
|---|---|---|
| Chicken (skinless, breast) | 193 +/− 27 | No |
| Chicken (drumstick, skin on) | 121 +/− 78 | No |
| Cooked Sweet corn on cob | 83 +/− 20 | No |
| Chili peppers (whole) | 53 +/− 18 | No |
| Red onions (sliced, raw) | 229 +/− 23 | Yes |
| Mushrooms (sliced, raw) | 122 +/− 18 | Yes |

-continued

| Test Article | Shear Force (N = 10, g/cm²) | Target Article Failure* |
|---|---|---|
| Mushroom (sliced, cooked) | 35 +/− 15 | Yes |
| Cherry tomatoes (whole) | 125 +/− 65 | No |
| Beefsteak tomato (sliced, raw) | 73 +/− 58 | Yes |
| Ham (sliced, deli) | 180 +/− 27 | No |
| Bacon (uncooked) | 98 +/− 36 | Yes (fat area) |
| Bacon (cooked) | 59 +/− 28 | Yes |
| Pepperoni (sliced) | 123 +/− 27 | No |
| Pineapple (sliced) | 298 +/− 33 | Yes |
| Jalapeno peppers (whole) | 59 +/− 26 | No |
| Green peppers (whole, waxed) | 72 +/− 29 | No |
| Meatballs (round, tangent contact) | 154 +/− 28 | Yes |
| Mozzarella (slice) | 197 +/− 9 | No |
| Italian hard cheese (Parmesan, slice) | 164 +/− 36 | No |
| Blue cheese (slice) | 93 +/− 22 | Yes |
| Rocket (arugula, fresh) | 57 +/− 18 | Yes |
| Oregano (fresh, leaf) | 62 +/− 7 | Yes |
| Shrimp (uncooked, with shell) | 21 +/− 4 | No |
| Shrimp (uncooked, without shell) | 142 +/− 35 | No |
| Mandarins (sections) | 67 +/− 18 | Yes |
| Eel (sushi grade, skin on) | 27 +/− 6 | No |
| Tofu | 82 +/− 46 | Yes |

*If slippage is due to test article disaggregation then YES, slippage due to microstructure NO Thus, although there have been described particular embodiments of the present invention of a new and useful MICROSTRUCTURE SOFT TISSUE GRAFT it is not intended that such references be construed as limitations upon the scope of this invention except as set forth in the following claims.

What is claimed is:

1. A soft tissue repair graft comprising:
a first layer comprising a biocompatible, non-bioabsorbable polymeric mesh having a first surface and a second surface;
a second layer comprising an anti-adhesion formation polymeric material;
a third layer comprising a microstructured surface, wherein the microstructured surface comprises a first microstructured pattern and a second microstructured pattern, the first microstructured pattern having at least a first microfeature and a second microfeature wherein the first and second microfeatures are configured hierarchically, the second microstructured pattern having a barbed microfeature configured to invasively engage a target surface, the first microstructured pattern being disposed about the microstructured surface at a first position, and the second microstructured pattern being disposed about the microstructured surface at a second position different from the first position;
wherein the second pattern is configured to distribute a force over the area of contact of the target surface when the force is exerted on the soft tissue repair graft to invasively engage the second pattern, and wherein no single microfeature of the second pattern exerts more than 0.025 kg/cm³ of the volume of the single microfeature when the soft tissue repair graft is separated from the target surface, and wherein the separation force exceeds 25 kg/cm² of the contact area between the soft tissue repair graft and target surface; and
wherein the second layer is attached to at least a portion of the first surface of the first layer and the third layer is attached to at least a portion of the second surface of the first layer.

2. The soft tissue repair graft of claim 1 wherein the anti-adhesion formation polymeric material comprises bioabsorbable material and the microstructured surface comprises a nonbioabsorbable polymeric material.

3. The soft tissue repair graft of claim 1 wherein the anti-adhesion formation polymeric material comprises a bioabsorbable polymeric material and the microstructured surface comprises a bioabsorbable polymeric material.

4. The soft tissue repair graft of claim 1 wherein the anti-adhesion formation polymeric material comprises a non-bioabsorbable polymeric material and the microstructured surface comprises a non-bioabsorbable polymeric material.

5. The soft tissue repair graft of claim 1 wherein the anti-adhesion formation polymeric material comprises a non-bioabsorbable polymeric material and the microstructured surface comprises a bioabsorbable polymeric material.

6. The soft tissue repair graft of claim 1 wherein the microstructured surface comprises a first bioabsorbable polymeric material, and wherein the first pattern comprises a second bioabsorbable polymeric material and the second pattern comprises the first bioabsorbable polymeric material.

7. The soft tissue repair graft of claim 1 wherein the microstructured surface comprises a non-bioabsorbable polymeric material, and wherein the first pattern comprises a bioabsorbable polymeric material and the second pattern comprises the non-bioabsorbable polymeric material.

8. The soft tissue repair graft of claim 1 wherein the third layer comprises fenestrations such that tissue growth from the target surface penetrates through the third layer fenestrations and into the first layer.

9. The soft tissue repair graft of claim 1, wherein the polymeric mesh comprises pores with a diameter between 0.5 mm and 6 mm.

10. The soft tissue repair graft of claim 1, wherein the polymeric mesh comprises warp knitted filament having a diameter of between 5 microns and 100 microns.

11. The soft tissue repair graft of claim 1, wherein the graft has a mass per unit area less than 300 g/m².

12. The soft tissue repair graft of claim 1, wherein the second layer is attached to at least a portion of the first surface of the first layer at attachment sites, the attachment sites comprising a first filament for attaching the first and second layers together, and wherein adjacent attachment sites are separated by a distance of between 1 mm and 20 mm.

13. The soft tissue repair graft of claim 12, wherein the third layer is attached to at least a portion of the second surface of the first layer at attachment sites, the attachment sites comprising a second filament for attaching the first and third layers together, and wherein adjacent attachment sites are separated by a distance of between 0.1 mm and 10 mm.

14. The soft tissue repair graft of claim 13, wherein the first filament is bioabsorbable.

* * * * *